US009835597B2

(12) United States Patent
Shreve et al.

(10) Patent No.: US 9,835,597 B2
(45) Date of Patent: Dec. 5, 2017

(54) DEVICE CAPABLE OF PRESSURIZATION AND ASSOCIATED SYSTEMS AND METHODS

(71) Applicant: Waters Technologies Corporation, Milford, MA (US)

(72) Inventors: Joshua A. Shreve, Franklin, MA (US); Kurt Joudrey, Newton, MA (US); John Angelosanto, North Attleboro, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 153 days.

(21) Appl. No.: 14/381,971

(22) PCT Filed: Mar. 7, 2013

(86) PCT No.: PCT/US2013/029556
§ 371 (c)(1),
(2) Date: Aug. 28, 2014

(87) PCT Pub. No.: WO2013/134483
PCT Pub. Date: Sep. 12, 2013

(65) Prior Publication Data
US 2015/0040992 A1    Feb. 12, 2015

Related U.S. Application Data

(60) Provisional application No. 61/607,919, filed on Mar. 7, 2012.

(51) Int. Cl.
*G01N 30/02* (2006.01)
*G01N 30/46* (2006.01)
(Continued)

(52) U.S. Cl.
CPC ........... *G01N 30/02* (2013.01); *B01D 15/163* (2013.01); *B01D 15/40* (2013.01); *F17C 1/00* (2013.01);
(Continued)

(58) Field of Classification Search
CPC ..... Y10T 137/87917; Y10T 137/87925; Y10T 137/87507; Y10T 137/86027;
(Continued)

(56) References Cited

U.S. PATENT DOCUMENTS 4,764,323 A * 8/1988 Al Ghatta ............... B29B 13/00
264/234
5,198,115 A    3/1993 Stalling et al.
(Continued)

OTHER PUBLICATIONS

Guiochon G, et al., Fundamental challenges and opportunities for preparative supercritical fluid chromatography. J Chromatogr A. Feb. 25, 2011;1218(8):1037-114.
(Continued)

*Primary Examiner* — Atif Chaudry
(74) *Attorney, Agent, or Firm* — Womble Bond Dickinson (US) LLP; Deborah M. Vernon; Heath T. Misley

(57) ABSTRACT

Exemplary embodiments are directed to devices, methods and systems capable of pressurization, generally involving a flow system that includes a pressurized reservoir, at least one pump including a pump control valve, an outlet port, a shut-off valve and a vent valve. The flow system is configured to be pressurized. The shut-off valve is disposed between the pressurized reservoir and the at least one pump. The vent valve is disposed between the at least one pump and the outlet port. The shut-off valve, the vent valve and the pump control valve of the at least one pump are configured to actuate in a coordinated manner to control a pressurization of the flow system. Exemplary embodiments are further directed to devices, methods and systems for column switch-
(Continued)

ing, generally including at least a first column, a second column and a column switching valve.

25 Claims, 7 Drawing Sheets

(51) Int. Cl.
  *B01D 15/40* (2006.01)
  *G01N 30/36* (2006.01)
  *B01D 15/16* (2006.01)
  *F17C 1/00* (2006.01)
  *G01N 30/32* (2006.01)
(52) U.S. Cl.
  CPC .......... *G01N 30/36* (2013.01); *G01N 30/466* (2013.01); *G01N 30/32* (2013.01); *G01N 2030/027* (2013.01); *Y02P 20/544* (2015.11); *Y10T 137/0396* (2015.04); *Y10T 137/86027* (2015.04); *Y10T 137/86035* (2015.04); *Y10T 137/87314* (2015.04); *Y10T 137/87507* (2015.04); *Y10T 137/87917* (2015.04); *Y10T 137/87925* (2015.04)
(58) Field of Classification Search
  CPC ............ Y10T 137/87314; G01N 30/02; G01N 30/466; G01N 30/36; G01N 2030/027; B01D 15/40; Y02P 20/544
  See application file for complete search history.

(56) References Cited

U.S. PATENT DOCUMENTS

| | | | |
|---|---|---|---|
| 5,234,599 A * | 8/1993 | Cortes .................. | G01N 30/463 210/198.2 |
| 5,360,320 A | 11/1994 | Jameson et al. | |
| 5,750,029 A * | 5/1998 | Houck .............. | B01D 11/0203 210/137 |
| 5,866,004 A | 2/1999 | Houck et al. | |
| 5,961,835 A * | 10/1999 | Sarrade .............. | B01D 11/0203 210/634 |
| 2012/0122705 A1* | 5/2012 | Ting ....................... | G01N 1/286 506/7 |
| 2013/0074614 A1* | 3/2013 | Holmes .............. | B01L 3/50825 73/864.01 |

OTHER PUBLICATIONS

International Search Report for PCT/US2013/29556 dated May 8, 2013.

\* cited by examiner

DEVICE CAPABLE OF PRESSURIZATION AND ASSOCIATED SYSTEMS AND METHODS

RELATED APPLICATION

This application is a National Stage Application of International Application No. PCT/US2013/029556, filed Mar. 7, 2013, which claims priority to U.S. Provisional Application No. 61/607,919, filing date Mar. 7, 2012. Each of the foregoing applications is incorporated herein by reference in its entirety.

TECHNICAL FIELD

The present disclosure is directed to devices capable of pressurization and associated systems and methods and, more particularly, to devices, systems and methods of pressurization of a flow system that provide improved control of the flow system pressurization and/or permit a depressurization of the flow system prior to column switching (e.g., chromatography systems).

BACKGROUND

Chromatographic techniques are important tools for the identification and separation of complex samples. The basic principle underlying chromatographic techniques is the separation of a mixture into individual components by transporting the mixture in a moving fluid through a retentive media. The moving fluid is typically referred to as the mobile phase and the retentive media is typically referred to as the stationary phase. The separation of the various constituents of the mixture is based on differential partitioning between the mobile and stationary phases. Differences in components' partition coefficient result in differential retention on the stationary phase, resulting in separation.

Conventionally, the methods of choice for chromatographic separations have been gas chromatography (GC) and liquid chromatography (LC). One major difference between GC and LC is that the mobile phase in GC is a gas, whereas the mobile phase in LC is a liquid. For example, in GC, a supply of inert carrier gas (mobile phase) is continually passed as a stream through a heated column containing porous sorptive media (stationary phase). A sample of the subject mixture is injected into the mobile phase stream and passed through the column, where separation of the mixture is primarily due to the differences in the volatile characteristics of each sample component at the temperature of the column. A detector, positioned at the outlet end of the column, detects each of the separated components as they exit the column. Although GC is typically a sensitive method of analysis, the high temperatures required in GC make this method unsuitable for high molecular weight biopolymers or proteins (heat will denature them), frequently encountered in biochemistry.

Conversely, LC is a separation technique in which the mobile phase is a liquid and does not require volatilization of the sample. Liquid chromatography that generally utilizes small packing particles and moderately high pressure is referred to as high-performance liquid chromatography (HPLC); whereas liquid chromatography that generally utilizes very small packing particles and high pressure is referred to as ultra-high performance liquid chromatography (UHPLC). In HPLC and UHPLC the sample is forced by a liquid at high pressure (the mobile phase) through a column that is packed with a stationary phase composed of irregularly or spherically shaped particles, a porous monolithic layer, or a porous membrane.

Because LC uses liquid as the mobile phase, LC techniques are capable of analyzing higher molecular weight compounds and, in some cases, LC can be used to prepare large scale batches of purified protein(s). However, in contrast, GC techniques are typically more sensitive and readily allow for the separation of single chiral materials. Thus, GC has conventionally been used to isolate and determine the relative purity of a chiral compound, e.g., by determining the enantiomeric excess (% ee) or the diastereomeric excess (% de) of a particular sample. As with most chromatographic techniques, the limiting factor in both GC and LC has been the ability to obtain and/or reproduce pure sample separations, each of which are typically dependent on the apparatus, methods, and conditions employed, e.g., flow rate, column size, column packing material, solvent gradient, etc.

Supercritical Fluid Chromatography is another chromatographic technique, which has typically been used in preparative applications. For every liquid substance there is a temperature above which it can no longer exist as a liquid, no matter how much pressure is applied. Likewise, there is a pressure above which the substance can no longer exist as a gas no matter how much the temperature is raised. These points are called the supercritical temperature and supercritical pressure, and define the boundaries on a phase diagram for a pure substance (FIG. 1). At this point, the liquid and vapor have the same density and the fluid cannot be liquefied by increasing the pressure. Above this point, where no phase change occurs, the substance acts as a supercritical fluid (SF). Thus, SF can be described as a fluid obtained by heating above the critical temperature and compressing above the critical pressure. There is a continuous transition from liquid to SF by increasing temperature at constant pressure or from gas to SF by increasing pressure at constant temperature.

The term SFC, while typically standing for Supercritical Fluid Chromatography, does not require or mean that supercritical conditions are obtained during or maintained throughout the separation. That is, columns do not have to be always operated in the critical region of the mobile phase. For example, in the event that the mobile phase includes a modifier (e.g., $CO_2$ and methanol as a modifier), the mobile phase is often in its subcritical region (e.g., a highly compressed gas or a compressible liquid rather than a supercritical fluid). In fact, as Guiochon et al note in section 2.3 of their review article entitled "Fundamental challenges and opportunities for preparative supercritical fluid chromatography" Journal of Chromatography A, 1218 (2011) 1037-1114: "It is obvious that SFC has very often been and still is run under subcritical conditions." Thus, the term SFC is not limited to processes requiring supercritical conditions.

Because SFC typically uses $CO_2$, SFC processes are inexpensive, innocuous, eco-friendly, and non-toxic. There is typically no need for the use of volatile solvent(s) (e.g., hexane). Finally, the mobile phase in SFC processes (e.g., $CO_2$ together with any modifier/additive as a SF, highly compressed gas, or compressible liquid) typically have higher diffusion constants and lower viscosities relative to liquid solvents. The low viscosity means that pressure drops across the column for a given flow rate is greatly reduced. The increased diffusivity means longer column length can be used.

SUMMARY

Exemplary embodiments of the present technology include devices, systems and methods which provide complete or substantially complete control of flow system pressurization and/or depressurization, especially in the event of column switching in a $CO_2$-based chromatography system.

In accordance with embodiments of the present technology, exemplary devices capable of pressurization and associated systems and methods are disclosed that involve a flow system that includes a pressurized reservoir, at least one pump including a pump control valve, an outlet port, a shut-off valve and a vent valve. The flow system can be configured to be pressurized. The shut-off valve is disposed between the pressurized reservoir and the at least one pump, i.e., downstream of the pressurized reservoir and upstream of the at least one pump. The vent valve is disposed between the at least one pump and the outlet port, i.e., downstream of the at least one pump and upstream of the outlet port. The shut-off valve, the vent valve and the pump control valve of the at least one pump are configured to actuate in a coordinated manner to control a pressurization of the flow system.

The flow system is a $CO_2$-based chromatography system, although it should be understood that alternative flow systems can be used. The pressurized reservoir can be, e.g., a $CO_2$ tank, compounds capable of performing separations and are liquids at pressures commonly used in LC, or the like. The outlet port of the flow system can be at least one of an exhaust and a waste port.

The pressurization of the flow system can be a positive pressurization or a depressurization. For example, the positive pressurization can pressurize the flow system with $CO_2$ and a solvent, e.g., methanol, ethanol, 2-methoxyethanol, isopropyl alcohol (IPA), dioxane or the like, to an operational pressure. In some embodiments, the solvents include one or more of the following additives: tetrahydrofuran (THF), trifluoracetic acid (TFA), methylene chloride, chloroform, heptane, acetic acid, propylamine, isopropylamine. In general, an additive makes up about 5% or less of the solvent. In embodiments, the solvent (including any additives), when combined with the CO2, makes up to about 55% of the combined flow streams. The operational pressure of the flow system can be in the range of between about 700 psi and 18,000 psi. In some embodiments, the range is between 1,400 psi and 8,000 psi (e.g., 1,500 psi and 6,000 psi). The depressurization of the system reduces the pressurization of the flow system to an atmospheric pressure.

The shut-off valve and the vent valve of the flow system can be configured to actuate into a closed position or an open position. The pump control valve of the at least one pump can be configured to actuate into a flow position or a vent position. In addition, the shut-off valve, the vent valve and the pump control valve of the at least one pump are in communication relative to each other. Thus, a positive pressurization of the flow system can be achieved upon actuation of the vent valve into the closed position, actuation of the shut-off valve into the open position and actuation of the pump control valve of the at least one pump into the flow position. On the other hand, a depressurization of the flow system can be achieved upon actuation of the shut-off valve into the closed position, actuation of the vent valve into the open position and actuation of the pump control valve of the at least one pump into the vent position.

In accordance with embodiments of the present disclosure, an exemplary method of managing pressurization is provided, generally involving a flow system that includes a pressurized reservoir, at least one pump including a pump control valve, an outlet port, a shut-off valve and a vent valve. The flow system is configured to be pressurized. The shut-off valve is disposed between the pressurized reservoir and the at least one pump, i.e., downstream of the pressurized reservoir and upstream of the at least one pump. The vent valve is disposed between the at least one pump and the outlet port, i.e., downstream of the at least one pump and upstream of the outlet port. The shut-off valve, the vent valve and the pump control valve of the at least one pump are configured to actuate in a coordinated manner to control a pressurization of the flow system.

The flow system can be, e.g., a $CO_2$-based chromatography system capable of positive pressurization and depressurization. The shut-off valve and the vent valve can be configured to actuate into a closed position or an open position and the pump control valve of the at least one pump is configured to actuate into a flow position or a vent position. In addition, the shut-off valve, the vent valve and the pump control valve of the at least one pump are in communication relative to each other.

The exemplary method of managing pressurization also includes actuating the vent valve into the closed position, actuating the shut-off valve into the open position and actuating the pump control valve of the at least one pump into a flow position to achieve positive pressurization of the flow system. The exemplary method furthers include actuating the shut-off valve into the closed position, actuating the vent valve into the open position and actuating the pump control valve of the at least one pump into a vent position to achieve a depressurization of the flow system.

In accordance with further embodiments of the present disclosure, an exemplary system of managing pressurization is provided, generally involving a flow system that includes a pressurized reservoir, at least one pump including a pump control valve, an outlet port, a shut-off valve and a vent valve. The flow system is configured to be pressurized. The shut-off valve can be disposed between the pressurized reservoir and the at least one pump, i.e., downstream of the pressurized reservoir and upstream of the at least one pump. The vent valve can be disposed between the at least one pump and the outlet port, i.e., downstream of the at least one pump and upstream of the outlet port. The exemplary system includes at least one processing device configured to actuate the shut-off valve, the vent valve and the pump control valve of the at least one pump in a coordinated manner to control a pressurization of the flow system. The at least one processing device can be further configured to maintain communication between the shut-off valve, the vent valve and the pump control valve of the at least one pump.

In accordance with another embodiment of the present disclosure, an exemplary device for column switching is provided that generally involves a flow system that includes a pressurized reservoir, at least one pump including a pump control valve, an outlet port, a shut-off valve, a vent valve and at least a first column and a second column. The flow system is configured to be pressurized. The shut-off valve is disposed between the pressurized reservoir and the at least one pump, i.e., downstream of the pressurized reservoir and upstream of the at least one pump. The vent valve is disposed between the at least one pump and the outlet port, i.e., downstream of the at least one pump and upstream of the outlet port. The at least first column and second column are disposed between the at least one pump and the vent valve, i.e., downstream of the at least one pump and upstream of the vent valve. The shut-off valve, the vent valve and the pump control valve of the at least one pump can be configured to actuate in a coordinated manner to control a pressurization of the flow system prior to and after switching between the at least first column and second column.

As previously discussed, the flow system can be a $CO_2$-based chromatography system and the pressurization of the $CO_2$-based chromatography system can be a positive pressurization or a depressurization. The exemplary device can include at least one column switching valve disposed between the at least one pump and the vent valve, i.e., downstream of the at least one pump and upstream of the vent valve. The at least one column switching valve is configured to control switching between the at least first column and second column. In addition, the at least one column switching valve is configured to actuate in a coordinated manner with the shut-off valve, the vent valve and the pump control valve of the at least one pump during switching between the at least first column and second column.

The shut-off valve and the vent valve can be configured to actuate into a closed position or an open position. The at least one column switching valve can be configured to actuate into a desired port position. The pump control valve of the at least one pump is configured to actuate into a flow position or a vent position. The shut-off valve, the vent valve, the at least one column switching valve and the pump control valve of the at least one pump are in communication relative to each other. A depressurization of the flow system can be achieved upon actuation of the shut-off valve into the closed position, actuation of the vent valve into the open position and actuation of the pump control valve of the at least one pump into a vent position. Switching between the at least first column and second column is achieved upon actuation of the at least one column switching valve into a desired port position after depressurization of the flow system has been achieved. A positive pressurization of the flow system can be achieved upon actuation of the vent valve into the closed position, actuation of the shut-off valve into the open position and actuation of the pump control valve of the at least one pump into a flow position.

In accordance with yet another embodiment of the present disclosure, an exemplary method of column switching is provided, generally involving providing a flow system that includes a pressurized reservoir, at least one pump including a pump control valve, an outlet port, a shut-off valve, a vent valve and at least a first column and a second column. The flow system is configured to be pressurized. The shut-off valve is disposed between the pressurized reservoir and the at least one pump, i.e., downstream of the pressurized reservoir and upstream of the at least one pump. The vent valve is disposed between the at least one pump and the outlet port, i.e., downstream of the at least one pump and upstream of the outlet port. The at least first column and second column are disposed between the at least one pump and the vent valve, i.e., downstream of the at least one pump and upstream of the vent valve.

The shut-off valve, the vent valve and the pump control valve of the at least one pump are configured to actuate in a coordinated manner to control a pressurization of the flow system prior to and after switching between the at least first column and second column. The exemplary method can include actuating the shut-off valve into the closed position, actuating the vent valve into the open position and actuating the pump control valve of the at least one pump into a vent position to achieve a depressurization of the flow system. Further, actuating the at least one column switching valve into a desired port position to switch between the at least first column and second column upon achieving the depressurization of the flow system can be performed. The exemplary method can further include actuating the vent valve into the closed position, actuating the shut-off valve into the open position and actuating the pump control valve of the at least one pump into a flow position to achieve a positive pressurization of the flow system.

In accordance with a further embodiment of the present disclosure, an exemplary system of column switching is provided, generally involving a flow system that includes a pressurized reservoir, at least one pump including a pump control valve, an outlet port, a shut-off valve, a vent valve and at least a first column and a second column. The flow system is configured to be pressurized. The shut-off valve can be disposed between the pressurized reservoir and the at least one pump, i.e., downstream of the pressurized reservoir and upstream of the at least one pump. The vent valve can be disposed between the at least one pump and the outlet port, i.e., downstream of the at least one pump and upstream of the outlet port. The at least first column and second column can be disposed between the at least one pump and the vent valve, i.e., downstream of the at least one pump and upstream of the vent valve. The exemplary system includes at least one processing device configured to actuate the shut-off valve, the vent valve and the pump control valve of the at least one pump in a coordinated manner to control a pressurization of the flow system prior to and after switching between the at least first column and second column. The at least one processing device can further be configured to maintain communication between the shut-off valve, the vent valve, the at least one column switching valve and the pump control valve of the at least one pump.

The systems, processes and methods of the present disclosure provide numerous advantages. For example, one or more embodiments of the present technology provide increased safety in $CO_2$-based chromatography applications. A pressurized system with $CO_2$ takes a long time to depressurize through the flow path. A pressurized flow system with a $CO_2$ solvent mix can be dangerous to anyone who breaks a fitting as it may spray the user. Embodiments described herein feature systems that vent every time flow is stopped to ensure an idle system is depressurized. To depressurize, shut-off and vent valves act in a coordinated manner (e.g., are controlled by the same controller.) Another advantage realized in chromatographic applications of the present technology is increased column life. For column switching, bring columns online or offline can result in backflow. By utilizing systems, process, and/or methods in accordance with the present technology, pressure in the system can be quickly lowered (vented) to an acceptable level before switching columns to prevent backflow.

BRIEF DESCRIPTION OF THE DRAWINGS

The foregoing and other features and advantages provided by the present disclosure will be more fully understood from the following description of exemplary embodiments when read together with the accompanying drawings, in which.

DESCRIPTION OF EXEMPLARY EMBODIMENTS

Figure 1:
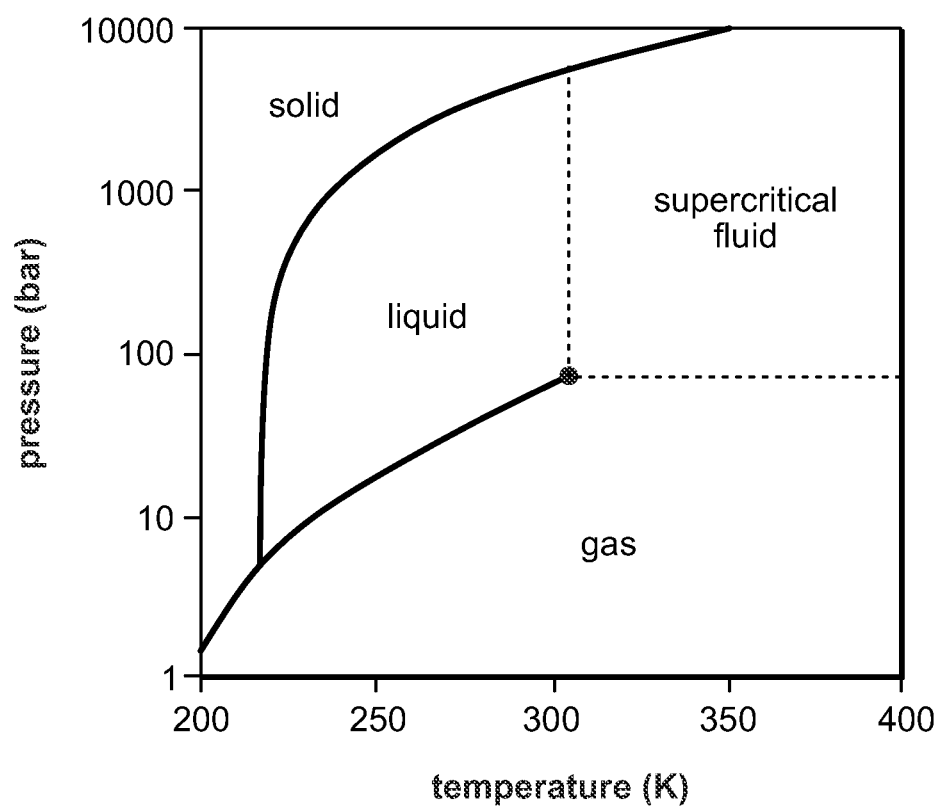
FIG. 1 is an exemplary graph of the physical state of a substance in relation to a temperature and pressure associated with the substance.

SFC can be adapted as a hybrid between HPLC and GC apparatuses, where the predominant modification is replacement of either the liquid or gas mobile phase with a supercritical fluid (or near supercritical fluid) mobile phase, such as with $CO_2$. In SFC, the mobile phase is initially pumped as a liquid or gas and is brought into the supercritical region by heating or pressurizing the mobile phase above its supercritical temperature/pressure prior to entry into a column. As the mobile phase passes through an injection valve, the sample is introduced into the supercritical stream, and the mixture is then transferred into a column. The mixture passes through the column (at supercritical or liquid state) and into the detector.

In general, the mobile phase in SFC processes have the ability to act both as substance carriers (like the mobile phases in GC), and dissolve substances readily (like the solvents used in LC). In addition to generally having lower viscosities and better diffusion profiles similar to those of certain gases, the mobile phase in SFC processes also generally have high densities and dissolving capacities similar to those of certain liquids. For example, SFs' high densities (0.2-0.5 $gm/cm^3$) provide for their remarkable ability to dissolve large, non-volatile molecules, e.g., supercritical or near supercritical $CO_2$ readily dissolves n-alkanes, di-n-alkyl phthalates, and polycyclic and aromatic compounds. Since the diffusion of solutes in a SFC mobile phase is about ten times greater than that in liquids (about three times less than in gases), this results in a decrease in resistance to mass transfer in the column and allows for fast high resolution separation. Also, the solvation strength of the mobile phase in SFC processes is directly related to the fluid density. Thus, the solubility of solids can be easily manipulated by making slight changes in temperatures and pressures.

Another important property of the mobile phase in SFC processes is that it provides high resolution chromatography at much lower temperatures. For example, an analyte dissolved in supercritical $CO_2$ can be recovered by reducing the pressure and allowing the sample to evaporate under ambient laboratory conditions. This property is useful when dealing with thermally unstable analytes, such as high molecular weight biopolymers or proteins.

The combination of one or more mechanical or column changes to an SFC instrument (e.g., a $CO_2$-based chromatography instrument) coupled with the inherent properties of the SFC itself, allows for the separation of both chiral and achiral compounds, and has become increasingly predominant in the field of preparatory separations for drug discovery and development. Despite considerable advances in SFC technology, there is a need to develop innovative methods and apparatuses that improve the use of SFC. Controlling and stabilizing the pressure in an SFC instrument by one or more process and/or improving one or more of the instrumental characteristics of the system, may lead to, amongst others, improved compound separation and efficiency.

For example, better resolution and increased flow rate would decrease cycle times (i.e., shorter cycle times) and allow for improved separation of both chiral and achiral compounds, and lead to an overall increase in laboratory efficiency; increased speed and throughput would decrease the amount of solvent and cost(s) associated with SFC; and the ability to further integrate SFC with other detection methods, such as Mass Spectrometry (MS), Flame Ionization Detectors (FID), and Ultraviolet/Visible (UV) detectors, would improve the mainstream use of SFC using a mobile phase including $CO_2$ as an eco-friendly, yet effective, alternative method for the fast, complete, and sensitive analysis of analytes.

In a conventional SFC system pressurized with a solvent, such as, e.g., $CO_2$, a combination of $CO_2$ and a modifier, such as methanol, or the like, requires an extensive about of time to depressurize through the flow path. In addition, the pressurized system can be dangerous to anyone who, e.g., breaks a fitting and/or is performing maintenance on these conventional systems, as the pressurized system can spray the $CO_2$ and/or solvent mix on the person. In terms of column switching, i.e., switching between at least a first column and a second column, backflow can be created in either the column coming offline and/or the column going online when the column switching valve is actuated while the column coming offline is still pressurized. The backflow through a pressurized column can fracture the column packing and can produce poor performance of the column and/or inaccurate results in these conventional systems.

Exemplary embodiments of the present technology include devices, systems and methods, which provide complete or substantially complete control of flow system pressurization and/or depressurization, especially in the event of column switching.

In accordance with embodiments of the present disclosure, exemplary devices capable of pressurization and associated systems and methods are disclosed that generally involve a flow system that includes a pressurized reservoir, at least one pump including a pump control valve, an outlet port, a shut-off valve and a vent valve. The flow system can be configured to be pressurized. The shut-off valve is disposed between the pressurized reservoir and the at least one pump, i.e., downstream of the pressurized reservoir and upstream of the at least one pump. The vent valve is disposed between the at least one pump and the outlet port, i.e., downstream of the at least one pump and upstream of the outlet port. The shut-off valve, the vent valve and the pump control valve of the at least one pump are configured to actuate in a coordinated manner to control a pressurization of the flow system.

In accordance with another embodiment of the present disclosure, exemplary devices and methods for column switching are provided that generally involves a flow system that includes a pressurized reservoir, at least one pump including a pump control valve, an outlet port, a shut-off valve, a vent valve and at least a first column and a second column. The flow system is configured to be pressurized. The shut-off valve is disposed between the pressurized reservoir and the at least one pump, i.e., downstream of the pressurized reservoir and upstream of the at least one pump. The vent valve is disposed between the at least one pump and the outlet port, i.e., downstream of the at least one pump and upstream of the outlet port. The at least first column and second column are disposed between the at least one pump and the vent valve, i.e., downstream of the at least one pump and upstream of the vent valve. The shut-off valve, the vent valve and the pump control valve of the at least one pump can be configured to actuate in a coordinated manner to control a pressurization of the flow system prior to and after switching between the at least first column and second column.

As used herein, the terms "downstream" and "upstream" refer to relative locations in a system flow, wherein upstream refers to being associated with an earlier portion of the system flow compared to later portion of the system flow and downstream refers to being associated with a later portion of the system flow compared to an earlier portion of the system flow.

Figure 2:
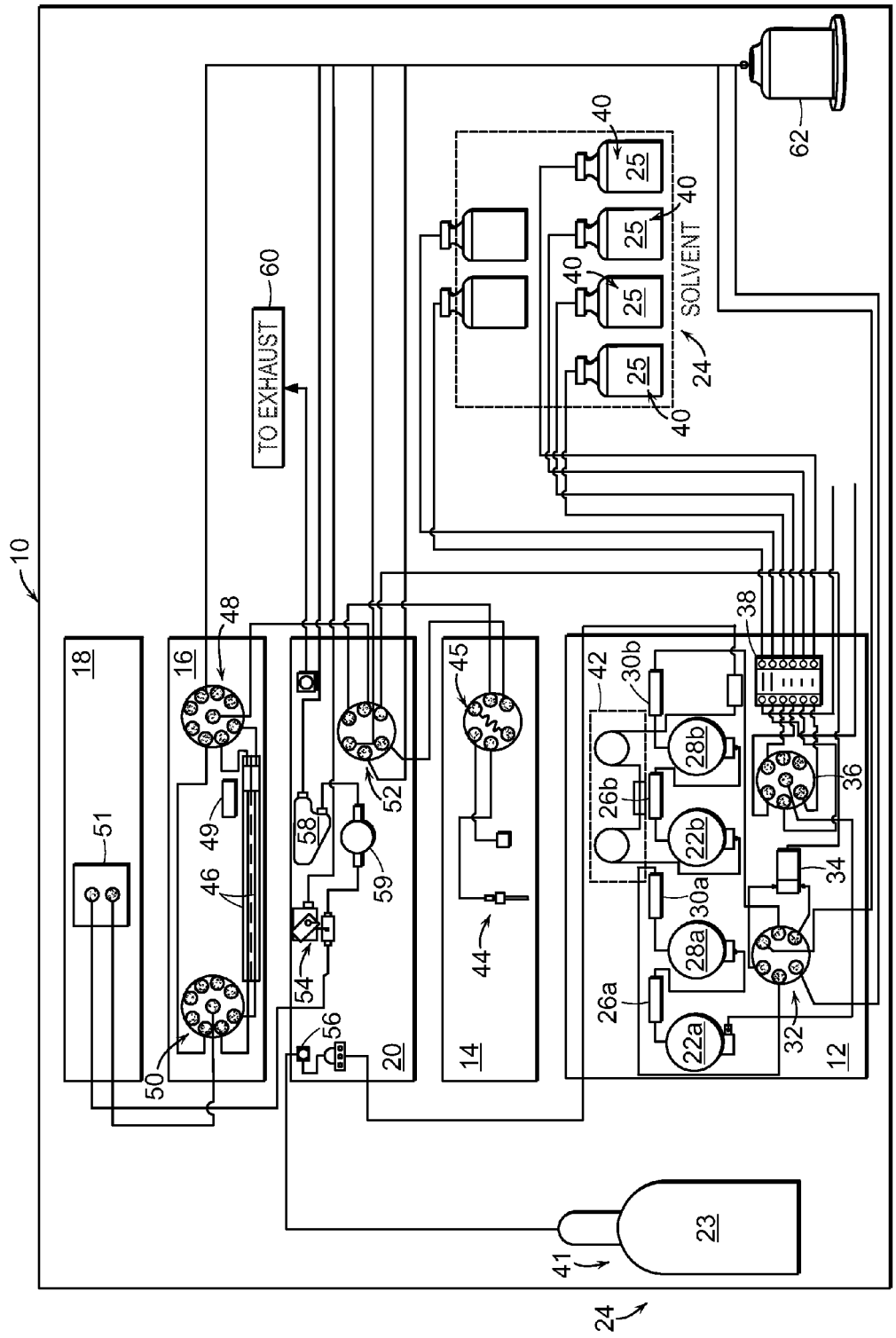
FIG. 2 is a block diagram of an exemplary pressurized flow system.

FIG. 2 is a block diagram of an exemplary pressurized flow system, which in the present embodiment is implemented as a $CO_2$-based chromatography system 10 (hereinafter "system 10"). While the present embodiment is illustrative of a $CO_2$-based chromatography system operated at or near supercritical conditions, those skilled in the art will recognize that exemplary embodiments of the present disclosure can be implemented as other pressurized flow systems and that one or more system components of the present disclosure can be implemented as components of other pressurized systems. System 10 can be configured to detect sample components of a sample using chromatographic separation in which the sample is introduced into a mobile phase that is passed through a stationary phase. System 10 can include one or more system components for managing and/or facilitating control of the physical state of the mobile phase, control of the pressure of the system 10, introduction of the sample to the mobile phase, separation of the sample into components, and/or detection of the sample components, as well as venting of the sample and/or mobile phase from the system 10.

Figure 3:
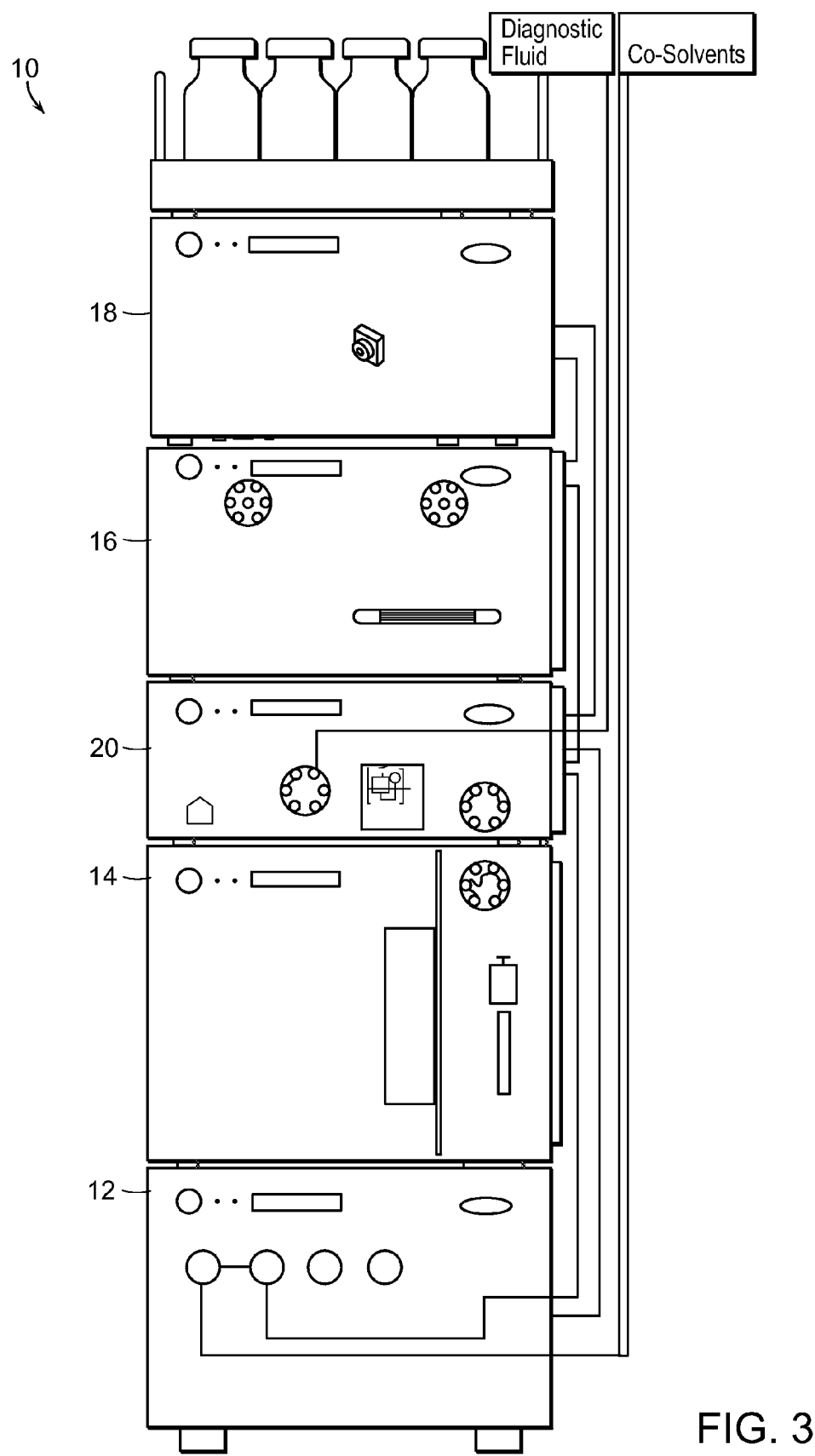
FIG. 3 is a block diagram of an exemplary arrangement of an embodiment of the system of FIG. 2.
Figure 4:
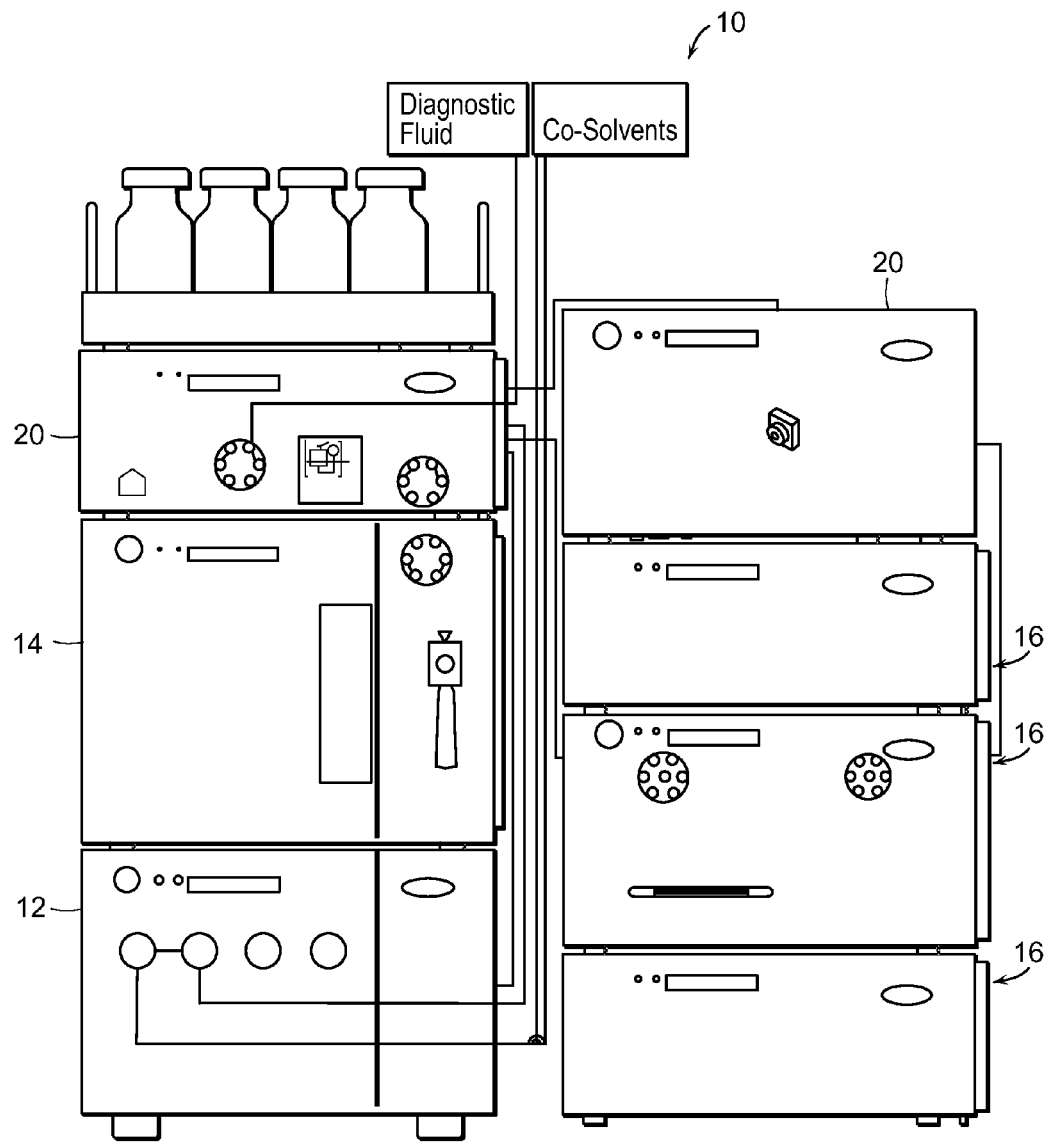
FIG. 4 is a block diagram of another exemplary arrangement of an embodiment of the system of FIG. 2.

In the present embodiment, system 10 can include a solvent delivery system 12, a sample delivery system 14, a sample separation system 16, a detection system 18 (e.g., a PDA detector), and a system/convergence manager 20. In some embodiments, the system components can be arranged in one or more stacks. As another example, in one embodiment, the system components of the system 10 can be arranged in a single vertical stack (FIG. 3). The system components of the system 10 can be arranged in multiple stacks (FIG. 4). Those skilled in the art will recognize that other arrangements of the components of the system 10 are possible. Furthermore, while embodiments of the system 10 have been illustrated as including system components 12, 14, 16, 18, and 20, those skilled in the art will recognize that embodiments of the system 10 can be implemented as a single integral unit, that one or more components can be combined, and/or that other configurations are possible.

The solvent delivery system 12 can include one or more pumps 22a and 22b configured to pump one or more solvents 24, such as mobile phase media 23 (e.g., carbon dioxide) and/or modifier media 25 (i.e., a co-solvent, such as, e.g., methanol), through the system 10 at a predetermined flow rate. For example, the pump 22a can be in pumping communication with the modifier media 25 to pump the modifier media 25 through the system 10, and the pump 22b can be in pumping communication with the mobile phase media 23 to pump the mobile phase media 23 through the system 10. An output of the pump 22a can be monitored by a transducer 26a and an output of the pump 22b can be monitored by a transducer 26b. The transducers 26a and 26b can be configured to sense the pressure and/or flow rate associated with the output of the solvent 24 from the pumps 22a and 22b, respectively. Each pump 22a and/or 22b further includes a pump control valve configured to be actuated into, e.g., a flow position, a block position, a vent position, and the like.

The outputs of the pumps 22a and 22b can be operatively coupled to an input of accumulators 28a and 28b, respectively. The accumulators 28a and 28b are refilled by the outputs of the pumps 22a and 22b, respectively, and can contain an algorithm to reduce undesired fluctuations in the flow rate and/or pressure downstream of the pumps 22a and 22b, which can cause detection noise and/or analysis errors on the system 10. An output of the accumulator 28a can be monitored by a transducer 30a and an output of the accumulator 28b can be monitored by a transducer 30b. The transducers 30a and 30b can be configured to sense pressure and/or flow rate at an output of the accumulators 28a and 28b, respectively. The outputs of the accumulators 28a and 28b can be operatively coupled to a multiport valve 32, which can be controlled to vent the solvent 24 (e.g., mobile phase media 23 and modifier media 25) being pumped by the pumps 22a and 22b and/or to output the solvent 24 to a mixer 34. The mixer 34 can mix the modifier media 25 and the mobile phase media 23 output from the pumps 22a and 22b, respectively (e.g., after first passing through the accumulators 28a and 28b) and can output a mixture of the mobile phase media 23 and the modifier media 25 to form a solvent stream (i.e., mobile phase) that flows through the system 10. The output of the mixer 34 can be operatively coupled to the system/convergence manager 20 as discussed in more detail below.

In exemplary embodiments, the solvent delivery system 12 can include a multiport solvent selection valve 36 and/or a degasser 38. The solvent selection valve 36 and/or the degasser 38 can be operatively disposed between an input of the pump 22a and solvent containers 40 such that the solvent selection valve 36 and/or the degasser 38 are positioned upstream of the pump 22a. The solvent selection valve 36 can be controlled to select the modifier media 23 to be used by the system 10 from one or more solvent containers 40 and the degasser 38 can be configured to remove dissolved gases from the media modifier 23 before the media modifier 23 is pumped through the system 10.

In exemplary embodiments, the solvent delivery system 12 can include a pre-chiller 42 disposed between an input of the pump 22b and a solvent container 41 such that the pre-chiller is disposed upstream of the input to the pump 22b and downstream of the solvent container 41. The pre-chiller 42 can reduce the temperature of the mobile phase media 23 before it is pumped through the system 10 via the pump 22b. In the present embodiment, the mobile phase media 23 can be carbon dioxide. The pre-chiller can decrease the temperature of the carbon dioxide so that the carbon dioxide is maintained in a liquid state (i.e., not a gaseous state) as it is pumped through at least a portion of the system 10. Maintaining the carbon dioxide in a liquid state can facilitate effective metering of the carbon dioxide through the system 10 at the specified flow rate.

The pumps 22a and 22b can pump the solvent 24 through the system 10 to pressurize the system 10 to a specified pressure, which may be controlled, at least in part, by the system/convergence manager 20. In exemplary embodiments, the system 10 can be pressurized to a pressure between about 700 psi and about 18,000 psi or about 1,400 psi and about 8,000 psi. In one embodiment, the system 10 can be pressurized to a pressure of about 6,000 psi. By pressurizing the system 10 at these pressure levels (such as those pressure levels described above), the solvent stream (i.e., mobile phase) can be maintained in a liquid state before transitioning to a supercritical fluid state or near supercritical state (e.g., highly-compressed gas or compressible liquid)

for a chromatographic separation in a column, which can be accomplished by raising the temperature of the pressurized solvent stream.

The sample delivery system 14 can select one or more samples to be passed through the system 10 for chromatographic separation and detection. The sample delivery system 14 can include a sample selection and injection member 44 and a multi-port valve 45. The sample selection and injection member 44 can include a needle through which the sample can be injected into the system 10. The multiport valve 45 can be configured to operatively couple the sample selection and injection member 44 to an input port of the system/convergence manager 20.

The sample separation system 16 can receive the sample to be separated and detected from the sample delivery system 14, as well as the pressurized solvent stream from the solvent delivery system 12, and can separate components of the sample passing through the system 10 to facilitate detection of the samples using the detection system 18. The sample separation system 16 can include one or more columns 46 disposed between an inlet valve 48 and an outlet valve 50. The one or more columns 46 can have a generally cylindrical shape that forms a cavity, although one skilled in the art will recognize that other shapes and configurations of the one or more columns is possible. The cavity of the columns 46 can have a volume that can at least partially be filled with retentive media, such as hydrolyzed silica, such as $C_8$ or $C_{18}$, or any hydrocarbon, to form the stationary phase of the system 10 and to promote separation of the components of the sample. The inlet valve 48 can be disposed upstream of the one or more columns can be configured to select which of the one or more columns 46, if any, receives the sample. The outlet valve 50 can be disposed downstream of the one or more columns 46 to selectively receive an output from the one or more columns 46 and to pass the output of the selected one or more columns 46 to the detection system 18. The columns 46 can be removably disposed between the valves 48 and 50 to facilitate replacement of the one or more columns 46 to new columns after use. In some embodiments, multiple sample separation systems 16 can be included in the system 10 to provide an expanded quantity of columns 46 available for use by the system 10 (FIG. 4).

In exemplary embodiments, the sample separation system 16 can include a heater 49 to heat the pressurized solvent stream 24 prior and/or while the pressured solvent stream 24 passes through the one or more columns 46. The heater 49 can heat the pressurized solvent stream to a temperature at which the pressured solvent transitions from a liquid state to a supercritical fluid state so that the pressurized solvent stream passes through the one or more columns 46 as a supercritical fluid.

Referring again to FIG. 2, the detection system 18 can be configured to receive components separated from a sample by the one or more columns 46 and to detect a composition of the components for subsequent analysis. In an exemplary embodiment the detection system 18 can include one or more detectors 51 configured to sense one of more characteristics of the sample components. For example, in one embodiment, the detectors 51 can be implemented as one or more photodiode arrays.

The system/convergence manager 20 can be configured to introduce a sample from the sample delivery system 14 into the pressurized solvent stream flowing from the solvent delivery system 12 and to pass the solvent stream and sample to the sample separation system 16. In the present embodiment, the system/convergence manager 20 can include a multiport auxiliary valve 52 which receives the sample injected by the sample delivery system 14 through a first inlet port and the pressurized solvent stream from the solvent delivery system 12 through a second inlet port. The auxiliary valve 52 can mix the sample and the solvent stream and output the sample and solvent stream via an outlet port of the multiport auxiliary valve 52 to an inlet port of the inlet valve 48 of the sample separation system 16.

The system/convergence manager 20 can also be configured to control the pressure of the system 10 and to facilitate cooling, heating and/or venting of the solvent from the system 10, and can include a vent valve 54, a shut off valve 56, a back pressure regulator 58, and a transducer 59. The vent valve 54 can be disposed downstream of the detection system 18 can be configured to decompress the system 10 by venting the solvent from the system 10 after the solvent has passed through the system 10. The shut-off valve 56 can be configured to disconnect the solvent supply from the inlet of the pump 22b of the solvent delivery system to prevent the solvent from being pumped through the system 10. In exemplary embodiments, an operation of the vent valve 54 and the shut-off valve 56 can be dependent on and/or coordinated relative to each other as described in more detail below. In exemplary embodiments, the shut-off valve 56 can be incorporated into the one or more pumps 22a and 22b or anywhere else in the system 10 if a controller is attached.

The back pressure regulator 58 can control the back pressure of the system 10 to control the flow of the mobile phase and sample through the column, to maintain the mobile phase in the supercritical fluid state (or, in some embodiments, in a near supercritical state, such as a highly-compressed gas or compressible liquid) as the mobile phase passes through the one or more columns 46 of the sample separation system 16, and/or to prevent the back pressure from forcing the mobile phase reversing its direction a flow through the one or more columns 46. Embodiments of the back pressure regulator 58 can be configured to regulate the pressure of the system 10 so that the physical state of the solvent stream (i.e., mobile phase) does not change uncontrollably upstream of and/or within the back pressure regulator 58. The transducer 59 can be a pressure sensor disposed upstream of the back pressure regulator 58 to sense a pressure of the system 10. The transducer 59 can output a feedback signal to a processing device which can process the signal to control an output of an actuator control signal from the processing device.

Figure 5:
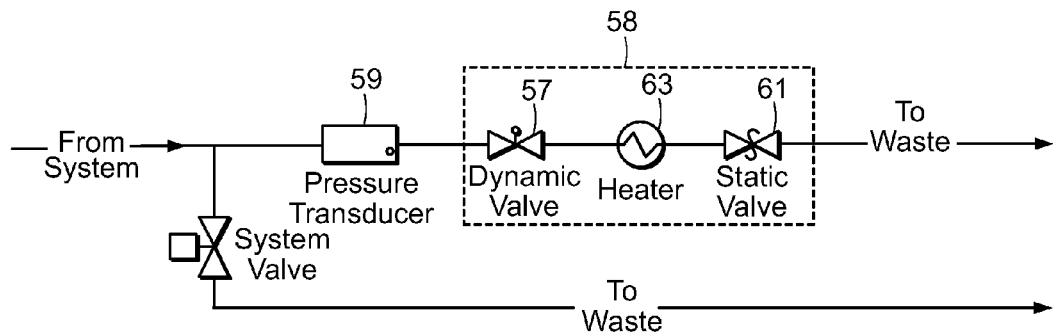
FIG. 5 is a flow diagram of a mobile phase through a system manager portion of the an exemplary embodiment of the pressurized flow system.

In exemplary embodiments, as shown in FIG. 5, the back pressure regulator 58 can include a dynamic pressure regulator 57, a static pressure regulator 61, and a heater 63. The static pressure regulator 61 can be configured to maintain a predetermined pressure upstream of the back pressure regulator 58. The dynamic pressure regulator 57 can be disposed upstream of the static pressure regulator 61 and can be configured to set the system pressure above the predetermined pressure maintained by the static regulator 61. The heater 63 can be disposed downstream of the dynamic pressure regulator 57 and can be disposed in close proximity to the static pressure regulator 61 to heat the solvent stream as it passes through the static pressure regulator 61 to aid in control of the physical state of the solvent as it passes through the static pressure regulator 61.

In summary, an exemplary operation of the system 10 can pump mobile phase media 23 and modifier media 25 at a specified flow rate through the system 10 as a solvent stream (i.e., mobile phase) and can pressurize the system 10 to a specified pressure so that the solvent stream maintains a liquid state before entering the sample separation system 16.

A sample can be injected into the pressurized solvent stream by the sample delivery system 14, and the sample being carried by the pressurized solvent stream can pass through the sample separation system 16, which can heat the pressurized solvent stream to transition the pressurized solvent stream from a liquid state to a supercritical fluid state. The sample and the supercritical fluid solvent stream can pass through at least one of the one or more columns 46 in the sample separation system 16 and the column(s) 46 can separate components of the sample from each other. The separated components can pass the separated components to the detection system 18, which can detect one or more characteristics of the sample for subsequent analysis. After the separated sample and solvent pass through the detection system 18, the solvent and the sample can be vented from the system 10 by the system/convergence manager 20.

In other embodiments, the system 10 described herein can also be used for preparatory methods and separations. Typical parameters, such as those described above, may be manipulated to achieve effective preparatory separations. For example, the system 10 described herein confers the benefit of exerting higher flow rates, larger columns, and column packing size, each of which contributes to achieving preparatory separation and function, while maintaining little or no variability in overall peak shape, peak size, and/or retention time(s) when compared to respective analytical methods and separations thereof. Thus, in one embodiment, the present disclosure provides $CO_2$-based chromatography systems 10 which are amendable to preparatory methods and separations with high efficiency and correlation to analytical runs.

With reference to FIG. 2 and, in particular, to the coordinated manner of operation between the vent valve 54 and the shut-off valve 56, the system 10 (the exemplary device capable of pressurization) includes a solvent 24, i.e., a pressurized reservoir, one or more pumps 22a and 22b (at least one pump) including a pump control valve, an outlet port, a shut-off valve 56 and a vent valve 54. The vent valve 54 and the shut-off valve 56 can be, e.g., solenoid valves. In other embodiments, the valves 54 and/or 56 can be voice coil valves or other actuator driven valves. The pump control valve can be actuated into, e.g., a flow position, a block position, a vent position, and the like. The outlet port can be, e.g., an exhaust port 60, a waste port 62, or the like. The shut-off valve 56 is disposed between the solvent 24 and the one or more pumps 22a and 22b, i.e., downstream of the solvent 24 and upstream of the one or more pumps 22a and 22b. It should be understood that the shut-off valve 56 can be positioned downstream of the one or more pumps 22a and 22b. However, this configuration requires an alternate method of venting and/or depressurizing the system 10 as the pump control valve of the one or more pumps 22a and 22b would not be capable of venting when the shut-off valve 56 has been actuated into a closed position. The vent valve 54 is disposed between the one or more pumps 22a and 22b and the outlet port, i.e., downstream of the one or more pumps 22a and 22b and upstream of the outlet port. The shut-off valve 56, the vent valve 54 and the pump control valve of the one or more pumps 22a and 22b can be configured to actuate in a coordinated manner to control a pressurization of the system 10.

The shut-off valve 56, the vent valve 54 and the pump control valve of the one or more pumps 22a and 22b are in communication relative to each other through the system/convergence manager 20, e.g., a processing device. The system/convergence manager 20 can be configured to monitor and/or actuate in a coordinated manner the system 10 components to control a pressurization of the system 10. Alternatively, the pressurization of the system 10 can be controlled manually for, e.g., maintenance of the system 10. In particular, the system 10 can be one of positively pressurized or depressurized. During operation of the system 10, e.g., chromatographic separation and detection, a positive pressurization is desired in the operational pressure range of between about 1,400 psi and about 8,000 psi. A lower operational pressure range can be implemented in conjunction with the system 10, so long as the pressure implemented is above the liquid pressure of the solvent 24 being used. Thus, system 10 can be operated with any solvent 24 in a liquid state. For example, if the solvent 24 is $CO_2$, a pressure of about 1,100 psi or greater (assuming a temperature of about 30° C.) should be implemented.

Figure 6:
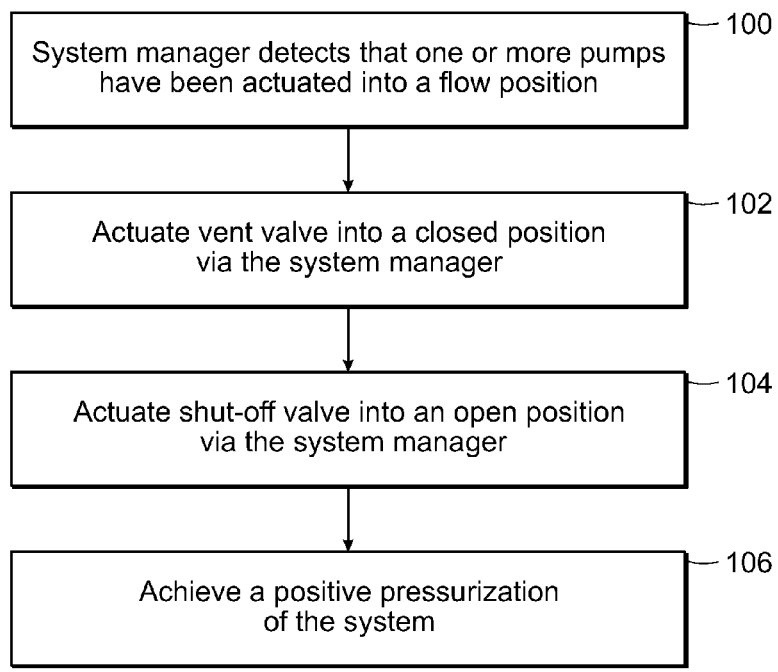
FIG. 6 is a block diagram for positively pressurizing an exemplary pressurized flow system.

Turning now to FIG. 6, a block diagram is provided for positively pressurizing the exemplary system 10. After the system/convergence manager 20 detects that one or more pumps 22a and 22b have been actuated to start flow (100), i.e., the pump control valve of the one or more pumps 22a and 22b has been actuated into a flow position, the system/convergence manager 20 actuates the vent valve 54 into a closed position (102) and actuates the shut-off valve 56 into an open position (104) to achieve the positive pressurization desired for operation of the system 10 (106). Thus, the vent valve 54, the shut-off valve 56 and the pump control valve of the one or more pumps 22a and 22b are monitored by a single processing device, i.e., the system/convergence manager 20, and the vent valve 54 and the shut-off valve 56 are actuated by a single processing device, i.e., the system/convergence manager 20, rather than separate processing and/or control devices as taught by the prior art. It should be understood that the coordinated manner of actuation depicted in FIG. 6 of the vent valve 54, the shut-off valve 56 and the pump control valve of the one or more pumps 22a and 22b can be in any order and/or sequence desired and is not required to occur in unison, although actuation in a substantially unison manner is preferred. Thus, the timing of actuation for the shut-off valve 56, the vent valve 54 and the pump control valve of the one or more pumps 22a and 22b can be staggered to create a substantially contemporaneous actuation of said components.

For example, the one or more pumps 22a and 22b can act as a "leader", e.g., transmitting to the system/convergence manager 20 whether a flow is being passed through the system 10. A flow can be pumped and/or passed through the system 10 when the one or more pumps 22a and 22b has been actuated to start flow, i.e., when the pump control valve of the one or more pumps 22a and 22b has been actuated into a flow position. In turn, the system/convergence manager 20 can actuate the shut-off valve 56 and the vent valve 54 into either an open position or a closed position accordingly. Thus, if the one or more pumps 22a and 22b transmit to the system/convergence manager 20 that a flow is being passed through the system 10, i.e., the one or more pumps 22a and 22b are in a flowing position (100), the system/convergence manager 20 can actuate the vent valve 54 into a closed position to seal the system 10 (102) and can further actuate the shut-off valve 56 into an open position (104) to permit the flow to pass into the system 10 to achieve a positive pressurization (106).

Alternatively, the system/convergence manager 20 can initially actuate the vent valve 54 into a closed position to prevent release of flow from the system 10 outlet ports (102). The system/convergence manager 20 can then actuate the shut-off valve 56 into an open position to permit flow from the solvent 24, i.e., the pressurized reservoir, to pass into the system 10 (104). The system/convergence manager 20 can then detect that one or more pumps 22a and 22b has been actuated to start flow, i.e., to pump the mobile phase media 23 and/or modifier media 25 through the system 10 (100) by actuating the pump control valve of the one or more pumps 22a and 22b into a flow position. In particular, the one or more pumps 22a and 22b can pump the mobile phase media 23 through the system 10 until a desired operational pressure has been reached (106). The desired operational pressure of the system 10 can further be maintained by the one or more pumps 22a and 22b until the operation, e.g., chromatographic separation and detection, has been completed.

As a further example, rather than actuating the vent valve 54 first, the system/convergence manager 20 can initially actuate the shut-off valve 56 into an open position to permit flow from the solvent 24, i.e., the pressurized reservoir, to pass into the system 10 (104). The vent valve 54 can then be actuated into a closed position to prevent release of flow from the system 10 outlet ports (102) and the one or more pumps 22a and 22b can pump the mobile phase media 23 and/or modifier media 25 through the system 10 (100) to achieve a desired operational pressurization (106). It should be understood that although a small portion of the mobile phase media 23 may initially exit and/or leak through the system 10 through the vent valve 54 prior to actuation of the vent valve into a closed position, the coordinated manner of the shut-off valve 56, the vent valve 54 and the pump control valve of the one or more pumps 22a and 22b can be sufficiently contemporaneous to ensure a large amount of mobile phase media 23 is not removed from the system 10 prior to closure of the vent valve 54. To prevent a loss and/or leak of the solvent 24 (e.g., the mobile phase media 23), the vent valve 54 can be actuated into a closed position prior to opening the shut-off valve 56.

Figure 7:
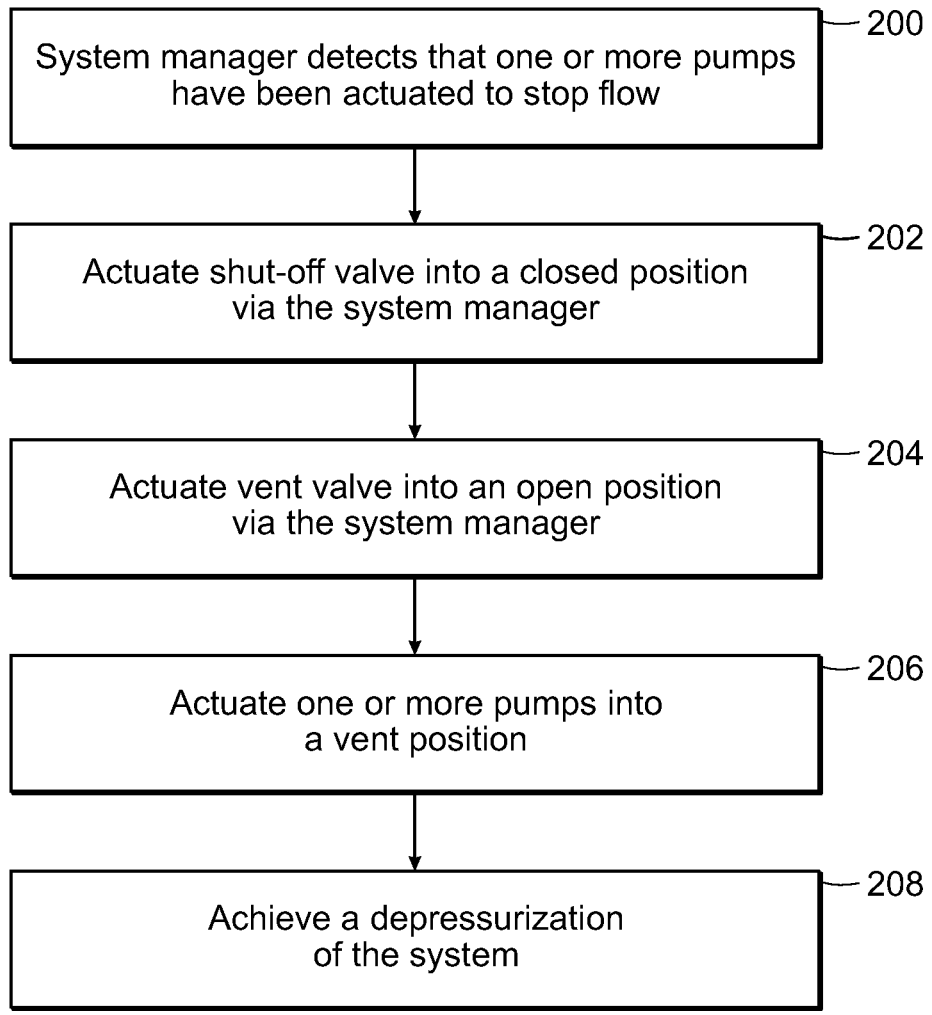
FIG. 7 is a block diagram for depressurizing an exemplary pressurized flow system.

Turning now to FIG. 7, a block diagram for depressurizing the exemplary system 10 is provided. Upon completion of the system 10 operation, e.g., chromatographic separation and detection, the idle system 10 can be automatically depressurized. In particular, when operation of the system 10 has been completed, the pump control valve of the one or more pumps 22a and 22b can be actuated to stop flow (200). The stopped flow can be transmitted/broadcast to and/or detected by the system/convergence manager 20 (200), which in turn can actuate the shut-off valve 56 into a closed position (202) and actuate the vent valve 54 into an open position (204). The one or more pumps 22a and 22b can then be actuated into a vent position (206), i.e., the pump control valve of the one or more pumps 22a and 22b can be actuated into a vent position, to depressurize the system 10 (208).

Similarly to the pressurization of the system 10, the depressurization of the system 10 can occur in a coordinated manner. It should be understood that the coordinated manner of actuation of the vent valve 54, the shut-off valve 56 and the pump control valve of the one or more pumps 22a and 22b can be in any order and/or sequence desired and is not required to occur in unison, although actuation in a substantially unison manner is preferred. Thus, for example, the coordinated manner of operation can be that the shut-off valve 56 is actuated into a closed position (202), the vent valve 54 is actuated into an open position (204) and the pump control valve of the one or more pumps 22a and 22b can be actuated into a vent position (206). On the other hand, the vent valve 54 can be actuated into an open position first (204), the shut-off valve 56 can then be actuated into a closed position (202) and the pump control valve of the one or more pumps 22a and 22b can be actuated into a vent position (206). It should be understood that although a small portion of the solvent 24 (e.g., mobile phase media 23) may initially exit the system 10 through the vent valve 54 prior to actuation of the shut-off valve 56 into a closed position, the coordinated manner of the shut-off valve 56, the vent valve 54 and the pump control valve of the one or more pumps 22a and 22b can be sufficiently contemporaneous to ensure a large amount of mobile phase media 23 is not removed from the system 10 prior to closure of the shut-off valve 56. To prevent an excess loss and/or leak of the mobile phase media 23, the shut-off valve 56 can be actuated into a closed position prior to opening the vent valve 54.

A depressurization, i.e., venting, of the system 10 can be performed automatically each time the flow of the mobile phase media 23 has been stopped through the system 10. Thus, an idle system 10 is not maintained in a pressurized condition. Rather, the idle system 10 is maintained in a depressurized condition. In addition, a flow LED light (not shown) can be activated and/or deactivated to indicate to a user that the system 10 has been depressurized and, e.g., is safe to perform maintenance on. Instead of waiting for the system 10 to depressurize through the flow path over time as taught by the prior art, a complete control of the pressurization of the exemplary system 10 permits a user to positively pressurize and/or depressurize the system 10 as desired in a short period of time.

Still with reference to FIG. 2, the system 10 (the exemplary device for column switching) includes a solvent 24, i.e., a pressurized reservoir, one or more pumps 22a and 22b (at least one pump) including a pump control valve, an outlet port, a shut-off valve 56, a vent valve 54 and one or more columns 46 (at least a first column and second column). The outlet port can be, e.g., an exhaust port 60, a waste port 62, or the like. The exemplary system 10 can include, e.g., up to six columns, although it should be understood that a greater amount of columns can be implemented. As previously described, the shut-off valve 56 is disposed between the solvent 24 and the one or more pumps 22a and 22b, i.e., downstream of the solvent 24 and upstream of the one or more pumps 22a and 22b. It should be understood that the shut-off valve 56 can be positioned downstream of the one or more pumps 22a and 22b. However, this configuration requires an alternate method of venting and/or depressurizing the system 10 as the pump control valve of the one or more pumps 22a and 22b would not be capable of venting when the shut-off valve 56 has been actuated into a closed position. The vent valve 54 is disposed between the one or more pumps 22a and 22b and the outlet port, i.e., downstream of the one or more pumps 22a and 22b and upstream of the outlet port. The one or more columns 46 is disposed between the one or more pumps 22a and 22b and the vent valve 54, i.e., downstream of the one or more pumps 22a and 22b and upstream of the vent valve. The shut-off valve 56, the vent valve 54 and the one or more pumps 22a and 22b can be configured to actuate in a coordinated manner to control a pressurization of the system 10 prior to and after switching between the one or more columns 46. It should be understood that the coordinated manner of the exemplary device for column switching, i.e., the system 10, is substantially similar to the coordinated manner of the exemplary device capable of pressurization discussed above.

The system 10 further includes at least one column switching valve, i.e., the inlet valve 48 and the outlet valve 50, disposed between the one or more pumps 22a and 22b and the vent valve 54, i.e., downstream of the one or more pumps 22a and 22b and upstream of the vent valve 54. The at least one column switching valve can be configured to control switching between the one or more columns 46 for, e.g., changing separation conditions. Further, the at least one column switching valve is configured to actuate in a coordinated manner with the shut-off valve 56, the vent valve 54 and the pump control valve of the one or more pumps 22a and 22b during switching between the one or more columns 46. The shut-off valve 56, the vent valve 54, the at least one column switching valve and the pump control valve of the one or more pumps 22a and 22b are in communication relative to each other through the system/convergence manager 20. Alternatively, the shut-off valve 56, the vent valve 54 and the pump control valve of the one or more pumps 22a and 22b can be in communication relative to each other, the shut-off valve 56 and the vent valve 54 can be actuated through the system/convergence manager 20, the pump control valve of the one or more pumps 22a and 22b can be actuated through a separate processing device, e.g., a pump manager (not shown), and the column switching valve is in communication with the system/convergence manager 20 and actuated through a separate processing device, e.g., a column manager (not shown).

The at least one column switching valve can be, e.g., a rotary valve configured to actuate into a desired port position. In particular, the column switching valve includes a plurality of ports which alter the fluidic path of the system 10 to a specific column of the one or more columns 46. Thus, the column switching valve can be actuated into a port position based on the desired one or more columns 46 to be implemented during operation of the system 10.

As discussed previously with respect to the prior art, a backflow can be created in either the column coming offline and/or the column going online when the column switching valve is actuated while the column coming offline is still pressurized. This backflow through a pressurized column can fracture the column packing, e.g., the retentive or stationary phase media, and can produce poor performance of the column, fracture of the column and/or inaccurate results. The exemplary system 10 configuration ensures a unidirectional flow through the one or more columns 46. In particular, during operation of the system 10, the operational flow of the mobile phase media 23 and any modifier 25 is pumped by the one or more pumps 22a and 22b in a single direction across the one or more columns 46. A column switching between the one or more columns 46 occurs in the system 10 after a depressurization of the system 10 has been achieved. The positioning of the one or more columns 46 downstream of the one or more pumps 22a and 22b and upstream of the vent valve 54 ensures that a depressurization of the system 10 creates a vent flow of the mobile phase media 23 in the substantially same direction as the operational flow. As would be understood by those of skill in the art, a depressurization and/or venting of the system 10 by the one or more pumps 22a and 22b forces the mobile phase media 23 (and any modifier media 25) along the operational flow path, across the one or more columns 46 and through the vent valve 54. The unidirectional flow across the one or more columns 46 increases the life of the one or more columns 46 due to the lack and/or reduction of backflow through the one or more columns 46.

In addition to the unidirectional flow, a switching between the one or more columns 46 after a depressurization of the system 10 has been achieved further ensures that a backflow is not created across the one or more columns 46. Thus, in addition to or alternative to controlling a pressurization of the system 10 in a coordinated manner during and after operation, the pressurization of the system 10 can further be controlled in a coordinated manner prior to and after switching between the one or more columns 46 to prevent damage to said columns. During operation, the exemplary device for column switching, i.e., the system 10, can achieve a positive pressurization to an operational pressure as previously discussed with respect to FIG. 6, e.g., actuating the vent valve 54 into the closed position, actuating the shut-off valve 56 into the open position and actuating the pump control valve of the one or more pumps 22a and 22b into a flow position. The coordinated manner of actuation can be in any order and/or sequence desired. It should be understood that the timing of actuation for the shut-off valve 56, the vent valve 54 and the pump control valve of the one or more pumps 22a and 22b can be staggered to create a substantially contemporaneous actuation of said components.

Figure 8:
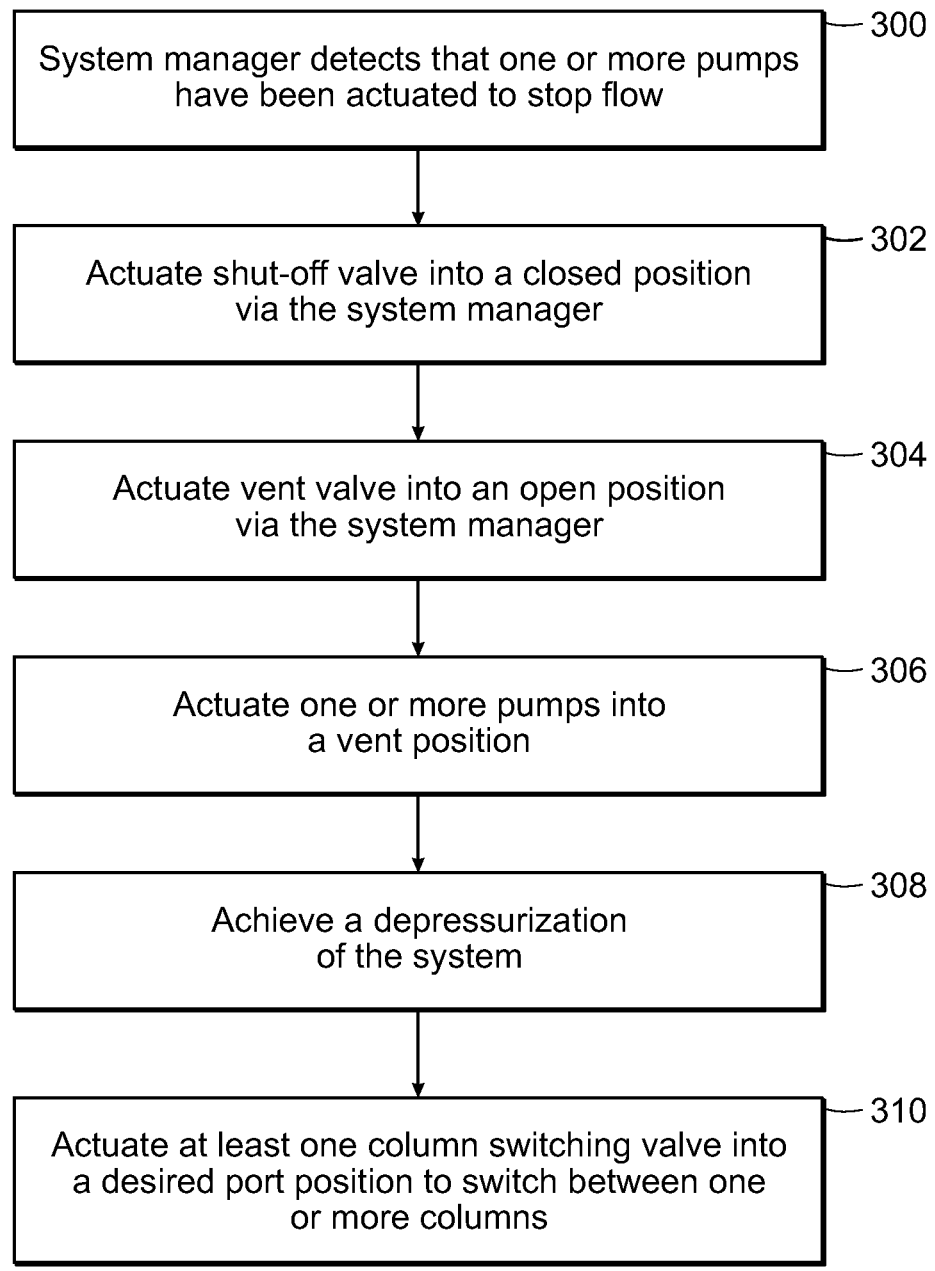
FIG. 8 is a block diagram for switching columns in an exemplary pressurizing flow system.

Turning now to FIG. 8, a block diagram is provided for column switching in an exemplary system 10. Prior to switching between the one or more columns 46, a depressurization and/or a pressure drop of the system 10 and, in particular, of the one or more columns 46, is achieved. The depressurization can be substantially similar to the depressurization discussed above with respect to FIG. 7. When the flow of the mobile phase media 23 (and any modifier media 25) has been stopped by the pump control valve of the one or more pumps 22a and 22b and the system/convergence manager 20 detects that the pump control valve of the one or more pumps 22a and 22b have been actuated to stop flow (300), a coordinated actuation of the shut-off valve 56 into the closed position (302) and an actuation of the vent valve 54 into the open position (304) can be performed by the system/convergence manager 20 to achieve a depressurization of the system 10 (308). In some embodiments, such as the one illustrated in FIG. 8, the pump control valve of the one or more pumps 22a and 22b can be actuated in a vent position (306) to aid in depressurization. FIG. 8 shows step (306) occurring in series with steps (302) and (304). In other embodiments, not shown, step (306) is eliminated or alternatively occurs in parallel with one or more of steps (302) and (304).

As previously noted, the coordinated manner of actuation can be in any order and/or sequence and can be staggered to ensure a substantially contemporaneous actuation of said components. The depressurization of the system 10 can occur in a unidirectional manner with respect to the operational flow direction. After the depressurization of the system 10 has reached an acceptable pressure range for column switching (308), e.g., between about atmospheric pressure and about average $CO_2$ tank pressure (e.g., about 800 psi), the system/convergence manager 20 can actuate the column switching valve into a desired port position (310). Alternatively, a column manager (not shown) can be in communication with the system/convergence manager 20 and can actuate the column switching valve into a desired port position. The column switching valve can thus rotate to change the flow between the one or more columns 46 based on the desired one or more columns 46 to be implemented in subsequent operation of the system 10 (310).

It should be understood that once the column switching valve has be actuated into a desired position and the one or more columns 46 have been switched, the system 10 can, e.g., remain idle in a depressurized condition, be positively pressurized to an operational pressure, and the like. The control of the system 10 pressurization and, thereby, the depressurization of the system 10 prior to switching the one or more columns 46, increases the life of one or more columns 46. In particular, the life of the one or more columns 46 is increased due to the lack of backflow through the system 10 and, thus, a reduction of packing fracture of the one or more columns 46. Enhanced performance and/or greater accuracy in results is therefore achieved with the exemplary system 10. Further, the control of pressurization of the exemplary system 10 offers enhanced safety and maintainability to a user.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the technology.

The invention claimed is:

1. A device capable of pressurization, comprising:
a flow system configured to be pressurized to a positive pressure that includes (i) a pressurized reservoir, (ii) a pump including a pump control valve, (iii) an outlet port, (iv) a shut-off valve disposed between the pressurized reservoir and the pump, (v) a vent valve disposed between the pump and the outlet port, and (vi) a controller communicatively coupled to the shut-off valve, the vent valve, and the pump control valve;
wherein the controller is configured to communicate with and actuate the shut-off valve, the vent valve, and the pump control valve in a coordinated and substantially unison manner to control pressurization of the flow system to the positive pressure; and
wherein pressurization of the flow system to the positive pressure with the controller includes the steps of (i) actuating the pump control valve into a flow position with the controller, (ii) when the pump control valve is actuated into and detected to be in the flow position, actuating the vent valve into a closed position with the controller, and (iii) when the vent valve is actuated into the closed position, actuating the shut-off valve into an open position with the controller.

2. The device of claim 1, wherein the flow system is a $CO_2$-based chromatography system and the pressurized reservoir is a $CO_2$ tank.

3. The device of claim 1, wherein the outlet port is at least one of an exhaust and a waste port.

4. The device of claim 1, wherein the flow system is configured to be depressurized from the positive pressure.

5. The device of claim 4, wherein depressurization of the flow system reduces the positive pressure of the flow system to an atmospheric pressure.

6. The device of claim 1, wherein the shut-off valve and the vent valve are configured to actuate into the closed position or the open position and the pump control valve of the pump is configured to actuate into the flow position or a vent position.

7. The device of claim 6, wherein the shut-off valve, the vent valve and the pump control valve of the pump are in communication relative to each other.

8. The device of claim 7, wherein a depressurization of the flow system from the positive pressure with the controller includes the steps of (i) actuating the shut-off valve into the closed position with the controller, (ii) when the shut-off valve is actuated into in the closed position, actuating the vent valve into the open position with the controller, and (iii) when the vent valve is actuated into the open position, actuating the pump control valve into the vent position with the controller.

9. The device of claim 1, wherein the flow system further includes a first column and a second column; wherein the first column and second column are disposed between the pump and the vent valve; and wherein the controller is configured to actuate the shut-off valve, the vent valve and the pump control valve of the pump in the coordinated and substantially unison manner to control the pressurization of the flow system to the positive pressure prior to switching between the first column and second column.

10. The device of claim 9, comprising a column switching valve disposed between the pump and the vent valve and configured to control switching between the first column and second column with the controller.

11. The device of claim 10, wherein the column switching valve is configured to be actuated with the controller in the coordinated and substantially unison manner with the shut-off valve, the vent valve and the pump control valve of the pump during switching between the first column and second column.

12. The device of claim 11, wherein the shut-off valve and the vent valve are configured to be actuated with the controller into the closed position or the open position, the column switching valve is configured to be actuated with the controller into a desired port position, and the pump control valve of the pump is configured to be actuated with the controller into the flow position or a vent position.

13. The device of claim 12, wherein the shut-off valve, the vent valve, the column switching valve and the pump control valve of the pump are in communication relative to each other.

14. The device of claim 13, wherein switching between the first column and second column is achieved upon actuation of the column switching valve into the desired port position after a depressurization of the flow system from the positive pressure has been achieved.

15. The device of claim 1, wherein the pump control valve is configured to be actuated by the controller between the flow position, a vent position, and a block position.

16. The device of claim 1, comprising an accumulator disposed downstream of the pump and configured to reduce fluctuations in a flow rate or pressure downstream of the pump, and comprising a transducer configured to detect the flow rate or pressure at an output of the accumulator.

17. A method of managing pressurization, comprising:
providing a flow system configured to be pressurized to a positive pressure that includes (i) a pressurized reservoir, (ii) a pump including a pump control valve, (iii) an outlet port, (iv) a shut-off valve disposed between the pressurized reservoir and the pump, (v) a vent valve disposed between the pump and the outlet port, and (vi) a controller, the controller being configured to actuate the shut-off valve, the vent valve, and the pump control valve in a coordinated and substantially unison manner to control pressurization of the flow system to the positive pressure;
actuating the pump control valve into a flow position with the controller;
when the pump control valve is actuated into and detected to be in the flow position, actuating the vent valve into a closed position with the controller; and
when the pump control valve is actuated into and detected to be in the flow position, actuating the shut-off valve into an open position with the controller.

18. The method of claim 17, wherein the shut-off valve and the vent valve are configured to actuate into the closed position or the open position and the pump control valve of the pump is configured to actuate into the flow position or a vent position, wherein the shut-off valve, the vent valve and the pump control valve of the pump are in communication relative to each other.

19. The method of claim 18, comprising (i) actuating the shut-off valve into the closed position with the controller, (ii) when the shut-off valve is actuated into the closed position, actuating the vent valve into the open position with the controller, and (iii) when the vent valve is actuated into the open position, actuating the pump control valve of the pump into a vent position with the controller to achieve a depressurization of the flow system from the positive pressure.

20. The method of claim 17, wherein the flow system further includes a first column and a second column; wherein the first column and second column are disposed between the one pump and the vent valve; and wherein the controller is configured to actuate the shut-off valve, the vent valve and the pump control valve of the pump in the coordinated and substantially unison manner to control the pressurization of the flow system to the positive pressure prior to switching between the first column and second column.

21. The method of claim 20, comprising a column switching valve disposed between the pump and the vent valve and configured to control switching between the first column and second column with the controller.

22. The method of claim 21, wherein the column switching valve is configured to be actuated with the controller in the coordinated and substantially unison manner with the shut-off valve, the vent valve and the pump control valve of the pump during switching between the first column and second column.

23. The method of claim 22, wherein the shut-off valve and the vent valve are configured to be actuated with the controller into the closed position or the open position, the column switching valve is configured to be actuated with the controller into a desired port position, and the pump control valve of the pump is configured to be actuated with the controller into the flow position or a vent position.

24. The method of claim 23, wherein the shut-off valve, the vent valve, the column switching valve and the pump control valve of the pump are in communication relative to each other.

25. The method of claim 23, comprising actuating the column switching valve with the controller into the desired port position to switch between the first column and second column upon achieving a depressurization of the flow system from the positive pressure.

* * * * *